(12) United States Patent
Rose et al.

(10) Patent No.: US 10,383,805 B2
(45) Date of Patent: *Aug. 20, 2019

(54) COMPOSITION AND PROCESS FOR SEMI-PERMANENT STRAIGHTENING OF HAIR

(71) Applicant: Kao Corporation, Tokyo, Japan (JP)

(72) Inventors: Burkhard Rose, Darmstadt (DE); Jonathan Wood, Weinheim (DE); Jörg Schneider, Griesheim (DE); Peter Bauer, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/770,603

(22) PCT Filed: Sep. 16, 2013

(86) PCT No.: PCT/EP2013/069126
§ 371 (c)(1),
(2) Date: Aug. 26, 2015

(87) PCT Pub. No.: WO2014/131470
PCT Pub. Date: Sep. 4, 2014

(65) Prior Publication Data
US 2016/0008251 A1    Jan. 14, 2016

(30) Foreign Application Priority Data
Feb. 28, 2013  (EP) ..................................... 13157225

(51) Int. Cl.
*A61Q 5/04* (2006.01)
*A61Q 5/06* (2006.01)
*A61K 8/49* (2006.01)
*A61K 8/41* (2006.01)
*A61K 8/46* (2006.01)
*A61K 8/81* (2006.01)
*A61K 8/36* (2006.01)
*A45D 2/00* (2006.01)
*A45D 7/04* (2006.01)
*A45D 7/06* (2006.01)
*A61K 8/06* (2006.01)
*A61K 8/365* (2006.01)

(52) U.S. Cl.
CPC ............ *A61K 8/4946* (2013.01); *A45D 2/001* (2013.01); *A45D 7/04* (2013.01); *A45D 7/06* (2013.01); *A61K 8/06* (2013.01); *A61K 8/36* (2013.01); *A61K 8/365* (2013.01); *A61K 8/416* (2013.01); *A61K 8/463* (2013.01); *A61K 8/817* (2013.01); *A61Q 5/04* (2013.01); *A61Q 5/06* (2013.01); *A61K 2800/30* (2013.01); *A61K 2800/882* (2013.01)

(58) Field of Classification Search
None
See application file for complete search history.

(56) References Cited

U.S. PATENT DOCUMENTS

| | | | | |
|---|---|---|---|---|
| 8,513,200 | B2* | 8/2013 | Dixon | A61K 8/042 514/20.7 |
| 2006/0140928 | A1* | 6/2006 | Bennett | A61K 38/51 424/94.61 |
| 2006/0222614 | A1* | 10/2006 | Buck | A61K 8/604 424/70.7 |
| 2009/0041701 | A1* | 2/2009 | Taylor | A61K 8/19 424/70.2 |
| 2010/0300471 | A1 | 12/2010 | Malle et al. | |
| 2012/0121529 | A1* | 5/2012 | Kruger | A61K 8/44 424/70.122 |
| 2012/0207689 | A1* | 8/2012 | Konno | A61K 8/046 424/62 |

FOREIGN PATENT DOCUMENTS

| | | |
|---|---|---|
| EP | 1 382 324 A2 | 1/2004 |
| EP | 1382324 * | 1/2004 |
| EP | 2 258 337 A1 | 12/2010 |
| GB | 1 416 564 A | 12/1975 |
| JP | H 02-276824 A | 11/1990 |
| WO | WO 00/00171 A1 | 1/2000 |
| WO | WO 2011/104282 A2 | 9/2011 |
| WO | WO 2012/010351 A1 | 1/2012 |
| WO | WO 2012/105985 A1 | 8/2012 |
| WO | WO 2014-072491 A1 | 5/2014 |

OTHER PUBLICATIONS

XP002703715: Database GNPD Mintel, Database accession No. 1692744, report of prior sale of "Moroccan Relaxing Treatment with Argan Oil", Jan. 2012.

XP002715458: "Commission Decision of May 8, 1996 establishing an inventory and a common nomenclature of ingredients employed in cosmetic products", Official Journal of the European Communities, L 132/1, I Jun. 1996 (Jun. 1, 1996), pp. I, 139, 141, 169, 222, 279, 384-385, 421, 520, URL:http://eurlcx. curopa.cu/LexUriScrv/LexUriServ.do?uri=O.J :L: 1996: 132:0001 :0684:EN :PDF [retrieved on Nov. 4, 2013].

XP002715459 "International Cosmetic Ingredient Dictionary and Handbook", 2012, Personal Care Products Council, vol. 2, pp. 2814-2815, entries "Quaternium-80" and "Quaternium-82"; p. 2814-p. 2815.

(Continued)

*Primary Examiner* — Jyothsna A Venkat
(74) *Attorney, Agent, or Firm* — Foley & Lardner LLP

(57) ABSTRACT

The present invention provides a hair straightening composition with improved ease of use, which leads to an enhanced smoothness of the straightened hair. The composition comprises at least one carboxylic acid of the formula (I) in combination with at least one quaternary ammonium compound having two long-chain hydrocarbon groups: R—CO—COOH Formula (I). In further aspects, the present invention concerns a process for semi-permanent straightening of the hair, utilizing said composition, the use of the composition for straightening hair, and a kit comprising the composition and a straightening iron.

3 Claims, No Drawings

(56) References Cited

OTHER PUBLICATIONS

XP009049226 Gao T et al: "Quaternium-91: A New Multifunctional Hair Conditioning Ingredient", Cosmetics & Toiletries, Wheaton, 11, Us, vol. 118, No. 5, May 1, 2003 (May 1, 2003), pp. 47-56.
European Search Report corresponding to Application No. 13157225.7, dated Dec. 6, 2013.
International Search Report and the Written Opinion of the International Searching Authority corresponding to Application No. PCT/EP2013/069126, dated Dec. 6, 2013.
"Commission Decision of May 8, 1996 establishing an inventory and a common nomenclature of ingredients employed in cosmetic products", Official Journal of the European Communities, L 132/1, Jun. 1, 1996 (Jun. 1, 1996), pp. 1, 2, 36, 48, 115, 139, 141, 150, 158, 169, 176, 253, 379, 383-385, 476.

\* cited by examiner

COMPOSITION AND PROCESS FOR SEMI-PERMANENT STRAIGHTENING OF HAIR

The present invention relates to a composition and a process for semi-permanent straightening of the hair.

BACKGROUND OF THE INVENTION

A known method for straightening curly or frizzy hair involves the use of straightening irons. The high temperature of the iron leads to a breakage of hydrogen bonds in the keratin of the hair, achieving a temporary straightening. The hydrogen bonds are formed again by the action of moisture, so that the hair reverts back to its original shape over the time because of air humidity, and the straightening effect vanishes after washing the hair.

The shape of the hair is largely determined by the disulfide bonds linking two cysteine moieties of the hair keratin. In order to achieve a more permanent shaping of the hair, known methods involve the cleavage of the disulfide bonds by the action of a sulfide- or thio group containing reducing agent. After the hair has been brought into the desired shape, new disulfide bonds are formed by applying an oxidizing agent such as hydrogen peroxide, thus fixing the shape of the hair. The use of such agents, however, may cause damage to the hair.

As an example for this kind of hair shaping treatment, reference is made to GB 1 416 564, describing reducing compositions comprising thioglycolates or thiolactates as reducing agents and fixing compositions comprising hydrogen peroxide as an oxidizing agent. The reducing compositions may further comprise a salt of an acid such as glyoxylic acid as a buffering agent.

As an alternative to the above-described two-step reduction and oxidation process, the disulfide bridges can be cleaved by the action of an alkaline agent such as sodium hydroxide at a pH of about 11 or higher. Under these conditions, the disulfide (or cystin) moiety can undergo a disproportionation reaction under the elimination of sulfur, and is cleaved into an alpha-beta-unsaturated dehydro-alanine moiety and a cysteine moiety. After the hair has been brought into the desired shape, the dehydro-alanin moieties and the cysteine moieties form thioether bonds and combine to lanthionine, stabilizing the straightened state of the hair. Since the disulfide or cystin moieties are converted into lanthionine moieties, this type of hair straightening process using an alkaline agent is also called lanthionization.

Both the two-stage reduction/oxidation method and the lanthionization method rely on a cleavage of the disulfide bonds and the formation of new bonds among the hair proteins, leading to an irreversible change of the shape of the hair. This means that these processes can achieve a permanent straightening, wherein the treated portion of the hair maintains its shape, and the straightening effect only vanishes because of the growth of the hair.

Recently, it has been found that carboxylic acids having a carbonyl group adjacent to the carboxy group, such as glyoxylic acid, which are known as a buffering agent in cosmetic compositions, may have a semi-permanent straightening effect when used in combination with mechanical straightening means.

In this respect, WO 2011/104282 describes a process for semi-permanent hair straightening, which involves applying a composition comprising an α-keto acid onto the hair, leaving the composition in contact with the hair for 15 to 120 minutes, drying the hair and straightening the hair with a straightening iron at a temperature of 200±50° C.

Furthermore, WO 2012/010351 describes a treatment for semi-permanent straightening of curly, frizzy or wavy hair by applying a solution of glyoxylic acid in combination with mechanical straightening, using a straightening iron at a temperature of 200±30° C. After the treatment, the hair is said to retain its shape for at least six consecutive washings.

EP 1 382 324 describes a foaming hair conditioner comprising a quaternary ammonium compound having an alkyl residue of 14 carbon atoms or higher ("monoalkyl quat") in combination with a C16-dialkyl quat and a C18-dialkyl quat at a certain ratio. The use of such a conditioner in connection with a straightening agent is not described, though.

SUMMARY OF THE INVENTION

The present invention relates to a hair straightening composition having a pH of 4 or less and comprising:
at least one carboxylic acid of the formula (I) and/or a hydrate thereof and/or a salt thereof:

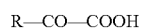
                    Formula (I)

wherein R is selected from hydrogen, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy; and at least one quaternary ammonium salt having two $C_5$-$C_{24}$ linear or branched, saturated or unsaturated hydrocarbon groups in the molecule, which may be the same or different and may be optionally substituted with one or more substituents selected from halogen, hydroxyl, amino and $C_1$-$C_4$ alkoxy.

The composition may be formulated as a one-part composition, or as a two-part composition comprising the parts A and B, which are stored separately and mixed prior to the application to the hair, wherein part A comprises the carboxylic acid of formula (I) and part B comprises at least one of a fragrance, a surfactant or a conditioning component. The quaternary ammonium salt having two $C_5$-$C_{24}$ hydrocarbon groups is contained in either or both of part A and part B, and is preferably contained in part B in case it has acid-sensitive groups. Improved fragrance stability is observed with two-part compositions.

In another aspect, the present invention relates to a process for semi-permanent hair straightening, comprising the following steps performed in this order:
(a) application of the above-described composition, which may be a one-part composition or a mixture of parts A and B of a two-part composition, as defined above, onto the hair;
(b) leaving the composition on the hair for 1 to 120 minutes;
(c) optionally rinsing off the hair;
(d) drying the hair;
(e) treating the hair with an iron having a surface temperature of 180±50° C.; and
(f) optionally rinsing off and/or shampooing the hair and drying.

In yet another aspect, the present invention relates to the use of the above-described composition for hair straightening, and to a kit comprising the composition and a straightening iron.

DETAILED DESCRIPTION OF THE INVENTION

Carboxylic acids of the formula (I), such as glyoxylic acid, have recently been found to provide remarkable semi-permanent straightening effects. However, there is a demand for improving the ease of use of these products and the smoothness of the straightened hair. It has not yet been described in the prior art that these aspects can be substantially improved by using a specific quaternary ammonium compound in combination with the acids of the formula (I).

The present inventors have found that the problem of improving the ease of use and the smoothness of the straightened hair can be solved by combining the carboxylic acid of formula (I) with a specific quaternary ammonium compound having two long-chain hydrocarbon groups.

Accordingly, the present invention provides a hair straightening composition, which comprises at least one carboxylic acid of the formula (I) in combination with at least one quaternary ammonium compound having two long-chain hydrocarbon groups, and a process for semi-permanent straightening of the hair utilizing said composition.

1. The Carboxylic Acid of Formula (I)

The straightening composition comprises at least one carboxylic acid of the following formula (I) as the active component for achieving the straightening effect:

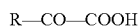  Formula (I)

wherein R is selected from hydrogen, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy.

As preferred examples, glyoxylic acid, pyruvic acid and 2-ketobutyric acid can be mentioned.

The carboxylic acid of Formula (I) may be comprised in the composition in its free acid form. The carbonyl group adjacent to the acid group of the acid may also be present in the hydrate form. Apart from the free acid form and the hydrate thereof, salts of the acid or the hydrate may also be used.

The hydrate of the acid of Formula (I) may be formed when providing the composition as an aqueous solution. For instance, glyoxylic acid (H—CO—COOH) in aqueous solution is almost quantitatively present as the hydrate (H—C(OH)$_2$—COOH). Besides, the hydrate may also condense to dimers.

A salt of the carboxylic acid of Formula (I) may also be used. As examples, alkali metal salts such as the sodium or potassium salt, alkaline earth metal salts such as the magnesium salt or the calcium salt and tertiary or quaternary ammonium salts may be mentioned.

In the present invention, glyoxylic acid, its salts and its hydrated form are the more preferred carboxylic acids of Formula (I).

The concentration of the at least one carboxylic acid of the Formula (I) and/or a hydrate thereof and/or salts thereof is usually in the range of 0.1 to 40%, preferably 0.5 to 40%, more preferably 2.5 to 40%, more preferably 0.5 to 30%, more preferably 1 to 25% and more preferably 2.5 to 20%, and even more preferably 2.5 to 14% by weight, based on the total weight of the straightening composition.

As discussed above, conventional permanent hair shaping/straightening techniques are based on the re-organization of the disulfide bridges and involve a cleavage of the disulfide bonds either by using a sulfur-based reducing agent or an alkali agent, followed by the shaping of the hair and the formation of new bonds (i.e., disulfide bonds formed by the action of an oxidizing agent or thioether bonds, respectively). In contrast to these permanent straightening methods, the present invention does not utilize cleavage of the disulfide bonds and fixing the bonds in the new shape. Therefore, the straightening composition of the present invention does not require the presence of sulfur-based reducing agents, and preferably is free of sulfur based reducing agents. However, up to 2% by weight calculated to the total of the composition of sulfur based reducing agents does not disturb the straightening performance of the compositions. Therefore, the treatment composition has less than 2% by weight of sulfur-based reducing agents, and preferably is free of sulfur-based reducing agents.

2. The Quaternary Ammonium Salt

The straightening composition of the present invention comprises at least one quaternary ammonium salt ("quat") having two $C_5$-$C_{24}$ linear or branched, saturated or unsaturated hydrocarbon groups in the molecule.

In accordance with the present invention, each of the $C_5$-$C_{24}$ linear or branched, saturated or unsaturated hydrocarbon groups may be attached to the cationic nitrogen atom of the quaternary ammonium compound either directly or via a spacer group, or may attached to the heterocyclic structure in case of a cyclic quaternary ammonium compound.

The two $C_5$-$C_{24}$ linear or branched, saturated or unsaturated hydrocarbon groups of the quaternary ammonium salt may be the same or different, and may optionally be substituted with at least one substituent selected from halogen, hydroxyl, amino and $C_1$-$C_4$ alkoxy. Preferably, the number of carbon atoms in the hydrocarbon groups is 8 to 22, more preferably 10 to 18.

In one embodiment, the quaternary ammonium salt is a non-cyclic quaternary ammonium salt of the following formula (II):

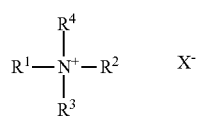  Formula (II)

wherein $R^1$ and $R^2$ are independently selected from the group consisting of:
- optionally substituted $C_5$-$C_{24}$ alkyl;
- optionally substituted $C_5$-$C_{24}$ alkenyl;
- optionally substituted $C_5$-$C_{24}$ alkynyl;
- groups of the formula R'—CO—NH—(CH$_2$)$_n$—, wherein R' is an optionally substituted $C_5$-$C_{24}$ alkyl, $C_5$-$C_{24}$ alkenyl or $C_5$-$C_{24}$ alkynyl group and n is an integer of 1 to 4; and groups of the formula R'—CO—O—(CH$_2$)$_n$—, wherein R' and n are the same as defined above;

the optional substituent(s) being selected from halogen, hydroxyl, amino and C$_1$-C$_4$ alkoxy;

R$^3$ and R$^4$, which may be identical or different, represent an alkyl group with 1 to 4 carbon atoms, which may optionally be substituted with one or more hydroxyl groups or ethylene oxide and/or propylene oxide adducts thereof, the average addition number being in the range of 1 to 4; and X$^-$ represents an anion such as chloride, bromide, methosulfate or ethosulfate.

Compounds of formula (II) wherein R$^1$ and R$^2$ represent alkyl are also referred to as "di-alkyl quats". As preferable examples for such compounds of formula (II), di-C$_{12}$-C$_{15}$-alkyl dimethylammonium or di-C$_{12}$-C$_{15}$-alkyl hydroxyethylmonium methylsulfonates may be mentioned.

In case one or both of R$^1$ and R$^2$ represent a group of the formula R'—CO—NH—(CH$_2$)$_n$— or R'—CO—O—(CH$_2$)$_n$—, n is preferably 2 and the R'—CO-moiety is preferably derived from a saturated or unsaturated C$_8$-C$_{22}$-fatty acid or a mixture of such fatty acids. As a preferable example for such a compound, dioleylethyl hydroxyethylmonium methosulfate (TETRANYL™ CO-40, commercially available from KAO CORPORATION) may be mentioned.

In another preferred embodiment, the quaternary ammonium salt is a cyclic compound of the imidazoline type, represented by the following formula (III):

Formula (III)

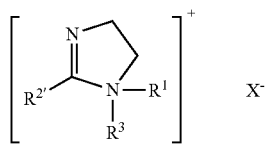

wherein R$^1$ and R$^3$ are the same as for the formula (II) defined above, and R$^{2'}$ represents a linear or branched C$_5$-C$_{24}$ alkyl, C$_5$-C$_{24}$ alkenyl or C$_5$-C$_{24}$ alkynyl group which may be optionally substituted with at least one substituent selected from halogen, hydroxyl, amino and C$_1$-C$_4$ alkoxy.

As apparent from formula (III), these imidazoline type quats may be considered as the quaternized cyclization product of an acyl amide compound of the formula R$^{2'}$—CO—NR$^1$—CH$_2$—CH$_2$—NH$_2$, wherein the NH$_2$ group undergoes a cyclization with the carbonyl group, and the resulting imidazoline ring is quaternized with R$^3$.

Preferably, R$^1$ in formula (III) represents a group of the formula R$^{1'}$—CO—NH—CH$_2$CH$_2$—, wherein the definition of R' is the same as R$^{2'}$. In this case, the compound of the formula (III) may be considered to be the quaternized cyclization product of diacylated diethylene triamine. The acyl groups R$^{1'}$—CO— and R$^{2'}$—CO— are preferably selected from saturated or unsaturated fatty acids and mixtures thereof.

As a preferable example thereof, Quaternium-91 (dibehenyl imidazoline quat, methosulfate salt) may be mentioned. The commercially available product Crodazosoft™ DBP-Q (manufactured by Croda Inc.) is a mixture of Quaternium-91, cetrimonium methosulfate and cetearyl alcohol, and may be preferably used for the present invention.

In the composition of the present invention, it is possible to use only a single type of the quaternary ammonium salt having two C$_5$-C$_{24}$ linear or branched, saturated or unsaturated hydrocarbon groups in the molecule, or a combination of two or more types.

The content of the at least one quaternary ammonium salt, such as the quaternary ammonium salt of the formula (II) and/or (III), in the composition is usually 0.01 to 15 wt %, more preferably 0.05 to 10 wt. %, and even more preferably 0.1 to 5 wt. %, based on the total weight of the straightening composition.

3. Surfactant

The straightening composition may comprise a surfactant. As the surfactant, any of a further cationic surfactant (in addition to the quaternary ammonium compound defined above), a nonionic surfactant, an amphoteric surfactant and an anionic surfactant can be used. It is also possible to use two or more types of surfactants in combination.

The further cationic surfactant is preferably a mono-long chain alkyl quaternary ammonium salt, having a C$_8$-C$_{24}$ alkyl residue and three C$_1$-C$_4$ alkyl residues.

In view of gliding of the iron on the hair, it is preferable to include at least one mono alkyl quaternary ammonium surfactant ("monoalkyl quat"), which is selected from the compounds with the general formula

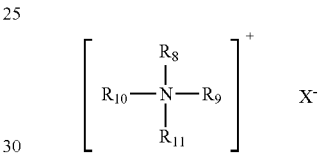

wherein R$_8$ is a saturated or unsaturated, branched or straight alkyl chain with 8-22 C atoms or

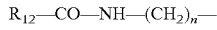

R$_{12}$—CO—NH—(CH$_2$)$_n$— wherein R$_{12}$ is a saturated or unsaturated, branched or straight alkyl chain with 7-21 C atoms and n is an integer of 1-4, or

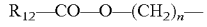

R$_{12}$—CO—O—(CH$_2$)$_n$— wherein R$_{12}$ is a saturated or unsaturated, branched or straight alkyl chain with 7-21 C atoms and n is an integer of 1-4, and R$_9$, R$_{10}$ and R$_{11}$ are independent from each other an alkyl group with 1 to 4 carbon atoms, hydroxyl alky chain with 1 to 4 carbon atoms, or ethoxy or propoxy group with a number of ethoxy or propoxy groups varying in the range of 1 to 4, and X is chloride, bromide, methosulfate or ethosulfate.

Suitable cationic surfactants are, for example, long-chain quaternary ammonium compounds which can be used alone or in admixture with one another, such as cetyl trimethyl ammonium chloride, myristyl trimethyl ammonium chloride, behentrimonium chloride, trimethyl cetyl ammonium bromide, stearyl trimethyl ammonium chloride, stearyl trimonium chloride and stearamidopropyltrimonium chloride.

Examples of the nonionic surfactant include polyoxy-C$_{1-4}$-alkylene C$_{8-24}$-alkyl ether, polyoxy-C$_{1-4}$-alkylene C$_{8-24}$-alkylene alkenyl ether, higher (C$_{12}$-C$_{24}$) fatty acid sucrose ester, polyglycerin C$_{8-24}$-fatty acid ester, higher (C$_{12}$-C$_{24}$) fatty acid mono- or diethanolamide, polyoxyethylene hardened castor oil, polyoxyethylene sorbitan C$_{8-24}$-fatty acid ester, polyoxyethylene sorbit C$_{8-24}$-fatty acid ester, C$_{8-24}$-alkyl saccharide surfactant, C$_{8-24}$-alkylamine oxide, and C$_{8-24}$-alkylamidoamine oxide.

Examples of the amphoteric surfactant include an imidazoline-based surfactant, a carbobetaine-based surfactant, an amidobetaine-based surfactant, a sulfobetaine-based surfactant, a hydroxysulfobetaine-based surfactant and an amidosulfobetaine-based surfactant.

Examples of the anionic surfactant include alkylbenzenesulfonate, alkyl or alkenyl ether sulfate, alkyl or alkenyl sulfate, olefin sulfonate, alkanesulfonate, saturated or unsaturated fatty acid salts, alkyl or alkenyl ether carboxylate, α-sulfo fatty acid salts, N-acylamino acid type surfactants, phosphoric acid mono- or diester type surfactants, and sulfosuccinate. Examples of the alkyl ether sulfate include polyoxyethylene alkyl ether sulfate. Examples of the counterion for the anionic residues of these surfactants include an alkalimetal ion such as sodium ion or potassium ion; an alkaline earth metal ion such as calcium ion or magnesium ion; an ammonium ion; and an alkanolamine having 1 to 3 alkanol groups each having 2 or 3 carbon atoms (for example, monoethanolamine, diethanolamine, triethanolamine, or triisopropanolamine).

The surfactant can be used singly or in combination of two or more kinds. When adding a surfactant to the straightening composition, the content thereof usually is 0.05 to 10% wt. %, more preferably 0.1 to 5 wt. %, based on the total weight of the straightening composition.

4. Conditioning Component

The straightening composition may optionally comprise a conditioning component suitable for application to the hair. The conditioning component is an oil or polymer which adheres to the hair and improves the feel and the manageability.

When using the conditioning component, the total content thereof is preferably 0.01 to 30 wt. %, more preferably 0.05 to 20 wt. %, and even more preferably 0.1% to 10 wt. %, based on the total weight of the straightening composition.

Examples of the conditioning component generally include cationic polymers, silicones, higher alcohols, and organic conditioning oils (for example, hydrocarbon oil, polyolefin and fatty acid ester). The composition may comprise a single type of conditioning component, or two or more in combination.

Cationic Polymers

A cationic polymer is a polymer having a cationic group or a group capable of being ionized into a cationic group, and in general, an amphoteric polymer acquiring net cationic charge is also included in the terminology. That is, the cationic polymer is a polymer containing an amino group or an ammonium group in a side chain of the polymer chain, or a polymer including a diallyl quaternary ammonium salt as a constituent unit, and examples thereof include cationized cellulose, cationic starch, cationic guar gum, a polymer or copolymer of a diallyl quaternary ammonium salt, and quaternized polyvinylpyrrolidone. Among these, from the viewpoint of softness, smoothness and easy finger-combing during shampooing, and easy manageability and moisture retention during drying, and from the viewpoint of stability of the agent, a polymer including a diallyl quaternary ammonium salt as a constituent unit, quaternized polyvinylpyrrolidone, and cationized cellulose are preferred, and a polymer or copolymer of a diallyl quaternary ammonium salt, and cationized cellulose are more preferred.

Specific examples of the polymer or copolymer of a diallyl quaternary ammonium salt include dimethyldiallylammonium chloride polymer (polyquaternium-6, for example, MERQUAT 100; Nalco Company), dimethyldiallylammonium chloride/acrylic acid copolymer (polyquaternium-22, for example, MERQUAT 280, MERQUAT 295; Nalco Company), and dimethyldiallylammonium chloride/acrylic acid amide copolymer (polyquaternium-7, for example, MERQUAT 550; Nalco Company).

Specific examples of the quaternized polyvinylpyrrolidone include quaternary ammonium salts synthesized from a copolymer of vinylpyrrolidone (VP) and dimethylaminoethyl methacrylate, and diethyl sulfate (polyquaternium 11, for example, GAFQUAT 734, GAFQUAT 755 and GAFQUAT 755N (all by ISP Japan, Ltd.)).

Specific examples of the cationized cellulose include a polymer of a quaternary ammonium salt obtained by adding glycidyltrimethylammonium chloride to hydroxyethylcellulose (polyquaternium-10, for example, RHEOGUARD G and RHEOGUARD GP (all by Lion Corp.), POLYMER JR-125, POLYMER JR-400, POLYMER JR-30M, POLYMER LR-400 and POLYMER LR-30M (all by Amerchol Corp.)), and a hydroxyethylcellulose/dimethyldiallylammonium chloride copolymer (polyquaternium-4, for example, CELQUAT H-100, CELQUAT L-200 (all by National Starch and Chemical Company)).

The cationic polymer may be used in combination of two or more kinds. Furthermore, the cationic polymer gives better effects when the content is increased, but an excessively high content of the cationic polymer may cause stability failure and a decrease in the viscosity of the agent alone or during mixing. From this viewpoint, and from the viewpoint of enhancing the feel to the touch, the content of the cationic polymer is preferably 0.001 to 20 wt %, more preferably 0.01 to 10 wt. %, and even more preferably 0.05 to 5 wt. %, based on the total weight of the straightening composition.

Silicones

In order to improve the feel of use, the straightening composition preferably contains a silicone. Examples of the silicone include dimethylpolysiloxane, and modified silicone (for example, amino-modified silicone, fluorine-modified silicone, alcohol-modified silicone, polyether-modified silicone, epoxy-modified silicone, polyoxazoline silicone (as described in JP Hei 2-276824), or alkyl-modified silicone), but dimethylpolysiloxane, polyether-modified silicone and amino-modified silicone are preferred.

The dimethylpolysiloxane may be any cyclic or non-cyclic dimethylsiloxane polymer, and examples thereof include SH200 series, BY22-019, BY22-020, BY11-026, B22-029, BY22-034, BY22-050A, BY22-055, BY22-060, BY22-083, FZ-4188 (all by Dow Corning Toray Co., Ltd.), KF-9008, KM-900 series, MK-15H, and MK-88 (all by Shin-Etsu Chemical Co., Ltd.).

The polyether-modified silicone may be any silicone having a polyoxyalkylene group, and the group constituting the polyoxyalkylene group may be an oxyethylene group or an oxypropylene group. More specific examples include KF-6015, KF-945A, KF-6005, KF-6009, KF-6013, KF-6019, KF-6029, KF-6017, KF-6043, KF-353A, KF-354A, KF-355A (all by Shin-Etsu Chemical Co., Ltd.), FZ-2404, SS-2805, FZ-2411, FZ-2412, SH3771M, SH3772M, SH3773M, SH3775M, SH3749, SS-280X series, BY22-008 M, BY11-030, and BY25-337 (all by Dow Corning Toray Co., Ltd.).

The amino-modified silicone may be any silicone having an amino group or an ammonium group, and examples thereof include an amino-modified silicone oil having all or a part of the terminal hydroxyl groups capped with a methyl group or the like, and an amodimethicone which does not have the terminals capped. A preferred example of the amino-modified silicone may be a compound represented by the following formula:

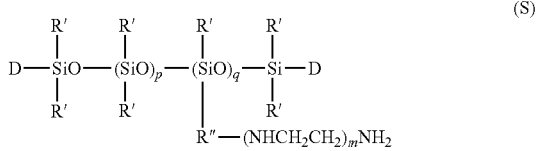

(S)

wherein R' represents a hydroxyl group, a hydrogen atom or $R^X$; $R^X$ represents a substituted or unsubstituted monovalent hydrocarbon group having 1 to 20 carbon atoms; D represents $R^X$, R"—$(NHCH_2CH_2)_mNH_2$, $OR^X$, or a hydroxyl group; R" represents a divalent hydrocarbon group having 1 to 8 carbon atoms; m represents a number from 0 to 3; p and q represent numbers, the sum of which is, as a number average, equal to or greater than 10 and less than 20,000, preferably equal to or greater than 20 and less than 3000, more preferably equal to or greater than 30 and less than 1000, and even more preferably equal to or greater than 40 and less than 800.

Specific examples of suitable commercially available products of the amino-modified silicone include amino-modified silicone oils such as SF8452C, SS-3551 (all by Dow Corning Toray Co., Ltd.), KF-8004, KF-867S, and KF-8015 (all by Shin-Etsu Chemical Co., Ltd.); and amodimethicone emulsions such as SM8704C, SM8904, BY22-079, FZ-4671, and FZ-4672 (all by Dow corning Toray Co., Ltd.).

The total content of these silicones in the straightening composition of the present invention is usually 0.1 to 20 wt. %, preferably 0.2% to 10 wt. % and more preferably 0.5 to 5 wt. %, based on the total weight of the straightening composition.

Oil Component

For improving the feel upon use, the straightening composition may also include an organic conditioning oil. The organic conditioning oil that is suitably used as a conditioning component is preferably a low-viscosity and water-insoluble liquid, and is selected from a hydrocarbon oil having at least 10 carbon atoms, a polyolefin, a fatty acid ester, a fatty acid amide, a polyalkylene glycol, and mixtures thereof. The viscosity of such an organic conditioning oil as measured at 40° C. is preferably 1 to 200 mPa·s, more preferably 1 to 100 mPa·s, and even more preferably 2 to 50 mPa·s. For the determination of the viscosity, a capillary viscometer may be used.

Examples of the hydrocarbon oil include a cyclic hydrocarbon, a linear aliphatic hydrocarbon (saturated or unsaturated), and a branched aliphatic hydrocarbon (saturated or unsaturated), and polymers or mixtures thereof are also included. The linear hydrocarbon oil preferably has 12 to 19 carbon atoms. The branched hydrocarbon oil includes hydrocarbon polymers, and preferably has more than 19 carbon atoms.

The polyolefin is a liquid polyolefin, more preferably a liquid poly-α-olefin, and even more preferably a hydrogenated liquid poly-α-olefin. The polyolefin used herein is prepared by polymerizing an olefin monomer having 4 to 14 carbon atoms, and preferably 6 to 12 carbon atoms.

The fatty acid ester may be, for example, a fatty acid ester having at least 10 carbon atoms. Examples of such a fatty acid ester include esters having a hydrocarbon chain derived from a fatty acid and an alcohol (for example, monoesters, polyhydric alcohol esters, or di- and tricarboxylic acid esters). The hydrocarbon group of these fatty acid esters may have another compatible functional group such as an amide group or an alkoxy group as a substituent, or the hydrocarbon group may be covalently bonded to those functional groups. More specifically, an alkyl and alkenyl ester of a fatty acid having a fatty acid chain having 10 to 22 carbon atoms, a carboxylic acid ester of an aliphatic alcohol having an aliphatic chain derived from an alkyl and/or alkenyl alcohol having 10 to 22 carbon atoms, and a mixture thereof are suitably used. Specific examples of these preferred fatty acid esters include isopropyl isostearate, hexyl laurate, isohexyl laurate, isohexyl palmitate, isopropyl palmitate, isopropyl myristate, decyl oleate, isodecyl oleate, hexadecyl stearate, decyl stearate, dihexadecyl adipate, lauryl lactate, myristyl lactate, cetyl lactate, oleyl stearate, oleyl oleate, oleyl myristate, lauryl acetate, cetyl propionate and dioleyl adipate.

Further suitable oil components are natural oils such as paraffin oil and natural triglycerides.

Suitable natural triglycerides are argan oil, shea butter oil, karite oil, olive oil, almond oil, avocado oil, *ricinus* oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, *passiflora* oil, black cumin oil, borage oils, grapeseed oil, hempseed oil, kukui nut oil, and rosehip oil.

The organic conditioning oil may be used in combination of two or more kinds, and the total concentration is typically in the range of 0.1 to 20 wt. %, preferably 0.2 to 10 wt. %, more preferably 0.5 to 5 wt. %, based on the total weight of the straightening composition.

Alcohols

From the viewpoint of improving the sense of touch and stability, the straightening composition may also contain a higher alcohol having 8 carbon atoms or more. Usually, the higher alcohol has 8 to 22 carbon atoms, and preferably 16 to 22 carbon atoms. Specific examples thereof include cetyl alcohol, stearyl alcohol, behenyl alcohol, and mixtures thereof.

The higher alcohol may be used in combination of two or more kinds, and the content thereof is typically 0.1 to 20 wt. %, preferably 0.2 to 10 wt. %, more preferably 0.5 to 5 wt. %, based on the total weight of the straightening composition.

Additionally polyols may suitably be comprised in the compositions. Examples of the polyalkylene glycol include polyethylene glycol and polypropylene glycol, and a mixture of the two may be used, or a copolymer of ethylene oxide and propylene oxide may also be used.

5. The Formulation of the Straightening Composition

The straightening composition may suitably be in the form of a solution, emulsion, cream, gel, paste and mousse.

In order to provide a sufficient straightening effect, the pH of the straightening composition is 4.0 or less, preferably in the range of 1 to 3.5, more preferably 1 to 3 and more preferably 1.5 to 3, as measured directly and at ambient temperature (25° C.). The pH of the composition may be adjusted using known alkaline solutions, preferably with sodium hydroxide solution.

Emulsion Formulations

The straightening composition is preferably formulated as an emulsion, preferably including a fatty alcohol such as cetearyl alcohol. In view of emulsion stability, a non-ionic or an additional cationic surfactant may optionally be added.

It is especially preferable to include a quaternary ammonium compound having one $C_5$-$C_{24}$ hydrocarbon group as the additional cationic surfactant. In this case, the ratio of the quaternary ammonium compound having two $C_5$-$C_{24}$ hydrocarbon groups and the quaternary ammonium compound having one $C_5$-$C_{24}$ hydrocarbon group is preferably within the range of 10:1 to 1:10, more preferably 5:1 to 1:5, more preferably 2:1 to 1:2. In order to improve the ease of use, one or more further conditioning components such as a silicone, preferably an amodimethicone may be added to the emulsion. Preferable emulsion formulations are described in the following.

Emulsion Formulation 1

| | |
|---|---|
| 2-20 wt. % | Glyoxylic acid |
| 0.1-2 wt. % | Di-$C_{12}$-$C_{15}$alkyldimethyl ammonium salt (e.g., chloride or methosulfate) |
| 0.2-5 wt. % | Mono-$C_{14}$-$C_{18}$alkyltrimethyl ammonium salt, preferably cetrimonium methosulfate |
| 1-5 wt. % | $C_{14}$-$C_{20}$ fatty alcohol, preferably cetearyl alcohol |

Emulsion Formulation 2

The emulsion composition may comprise a diacyloxyalkyl quat such as dioleylethyl hydroxyethylmonium methosulfate (TETRANYL™ CO-40) as an alternative to the dialkyl quat:

| | |
|---|---|
| 2-20 wt. % | Glyoxylic acid |
| 0.1-2 wt. % | Diacyloxyalkyl quat, preferably TETRANYL ™ CO-40 |
| 0.2-5 wt. % | Mono-$C_{14}$-$C_{18}$alkyltrimethyl ammonium salt, preferably Cetrimonium methosulfate |
| 1-5 wt. % | $C_{14}$-$C_{20}$ fatty alcohol, preferably cetearyl alcohol |

Emulsion Formulation 3

Another preferable type of formulation utilizes an imidazoline type quat of the formula (III), such as quaternium-91:

| | |
|---|---|
| 2-20 wt. % | Glyoxylic acid |
| 0.1-2 wt. % | imidazoline type quat preferably quaternium-91 |
| 0.2-5 wt. % | Mono-$C_{14}$-$C_{18}$alkyltrimethyl ammonium salt, preferably cetrimonium methosulfate |
| 1-5 wt. % | $C_{14}$-$C_{20}$ fatty alcohol, preferably cetearyl alcohol |

The emulsion formulations 1-3 may optionally comprise further ingredients such as additional surfactants and/or conditioning components. Cosmetically acceptable additives such as preservatives, dyes, and fragrances may be added if desired. The balance is water. The pH of the emulsion formulations 1-3 is adjusted to 1.5 to 2.5 using a base such as sodium hydroxide.

Gel Emulsions

Gel emulsions may be formulated by further adding a polymeric thickening agent to an emulsion formulation such as the Formulation Examples 1-3 described above.

Preferable polymeric thickening agents include anionic polysaccharides such as alginate, pectinate, xanthan, hydroxypropyl xanthan or dehydroxanthan, non-ionic polysaccharides such as cellulose ethers (e.g., methylcellulose, hydroxyethylcellulose (HEC), methyl hydroxyethylcellulose (MHEC), ethyl hydroxyethylcellulose (EHEC), methyl ethyl hydroxyethylcellulose (MEHEC)), starch or dextrins, and cationic or amphoteric polymers such polyquaternium-37 or the ones described above as conditioning agents. Among these polymers, xanthan, hydroxypropyl xanthan and dehydroxanthan are especially preferable.

The viscosity of such gel emulsions is typically within the range of 1,000 to 25,000, preferably 2500 to 15,000 mPa*s, as measured at 20° C. with a Brookfield viscometer (e.g., at 10 rpm with an appropriated spindle). The concentration of the polymeric thickening agent depends on the type of the agent and the desired viscosity, and is typically within the range of 0.01 to 15 wt. %, preferably 0.05 to 10 wt. %, more preferably 0.1 to 5 wt. %, and even more preferably 0.5 to 2 wt. % based on the weight of the straightening composition.

Preferable gel emulsion formulations are described in the following.

Gel Emulsion Formulation 1

| | |
|---|---|
| 5-20 wt. % | Glyoxylic acid |
| 0.1-2 wt. % | Di-$C_{12}$-$C_{15}$alkyldimethyl ammonium salt (e.g., chloride or methosulfate) |
| 0.2-5 wt. % | Mono-$C_{14}$-$C_{18}$alkyltrimethyl ammonium salt, preferably cetrimonium methosulfate |
| 1-5 wt. % | $C_{14}$-$C_{20}$ fatty alcohol, preferably cetearyl alcohol |
| 0.1-1 wt. % | thickening agent, preferably Xanthan gum, hydroxypropyl xanthan gum or dehydroxanthan gum |

The gel emulsion formulations 1 may optionally comprise further ingredients such as additional surfactants and/or conditioning components. Cosmetically acceptable additives such as preservatives, dyes, and fragrances may be added if desired. The balance is water. The pH of the gel emulsion formulations 1-3 is adjusted to 1.5 to 2.5 using a base such as sodium hydroxide.

Two-Component Formulations

In case it is desired to include compounds such as fragrances or surfactants and/or conditioning components which comprise acid-sensitive groups, it is possible that the storage stability at the above-described pH values is diminished. Besides, it is also possible that fragrance compounds undergo undesired reactions with the carbonyl group of the carboxylic acid of formula (I), which may lower the storage stability.

In order to avoid such problems, it may be preferable in these cases to formulate the straightening composition as a two-part system, comprising the parts A and B, which are stored separately and mixed prior to the application to the hair.

Part A comprises the carboxylic acid of the formula (I), while part B comprises at least one of a fragrance, a surfactant and a conditioning agent. The quaternary ammonium compound having two $C_5$-$C_{24}$ hydrocarbon groups and, optionally, thickeners, acid insensitive surfactants and conditioning agents may be added to part A, to part B or to both parts. An ester group containing quaternary ammonium compound such as a diacyloxyalkyl quat (e.g., TETRANYL™ CO-40) is preferable included in part B.

The pH of part B is adjusted such that the ingredients have sufficient storage stability, typically above 4 and usually within the range of 4 to 8, while the pH of part A is less than 4, usually within the range of 1 to 3.5. The final pH after mixing of parts A and B is 4 or lower, preferably 1 to 3.5. The parts A and B are mixed at a predefined ratio, e.g., 1:1, prior to use.

6. Hair Treatment Process

The hair treatment process of the present invention achieves a semi-permanent straightening of the hair, utilizing the acid of formula (I) such as glyoxylic acid as the active agent. The straightening effect of this process is not achieved by cleaving the disulfide bonds by reduction or the action of strong alkali. Accordingly, the usage of a reducing composition or an alkaline relaxer (lanthionization agent) is not required.

In step (a) of the process of the present invention, the straightening composition is applied to the hair. The application weight ratio of hair to composition is 0.5:2 to 2:0.5, preferably 0.5:1 to 1:0.5, more preferably about 1:1.

Subsequent to the application, the straightening composition is left on the hair for 1 to 120 minutes, preferably 5 to 90 minutes, more preferably 10 to 60 minutes and more preferably 15 to 45 minutes at a temperature of 45° C. or below, preferably at ambient temperature (step (b)). Then, the straightening composition is optionally rinsed off from hair (step (c)).

In subsequent step (d), the hair is dried in order to avoid an excessive steam generation in the subsequent step of treating the hair with the iron. Typically, a hair dryer is used for this purpose. It is preferable to dry the hair under continuous combing in order to prevent entanglement of the hair.

Subsequent to the drying, the hair is treated with an iron having a surface temperature of 180±50° C., preferably 170 to 200° C. A usual straightening iron may be used for this purpose (step (e)). Finally, the hair may optionally be rinsed off with water and/or shampooed and dried again (step (f)).

EXAMPLES

The present invention is now illustrated by the following non-limiting examples.

Example 1

A straightening composition in gel/emulsion form was prepared by mixing the following ingredients:

| | |
|---|---|
| Glyoxylic Acid | 10 wt. % |
| Cetearyl Alcohol | 2.18 wt. % |
| Dehydroxanthan Gum | 0.4 wt. % |
| Cetrimonium Methosulfate | 0.85 wt. % |
| Quaternium-91 | 0.27 wt. % |
| Water | ad. 100 wt. % |

The pH was adjusted to 2.0 using sodium hydroxide.

Example 2

A straightening composition in gel/emulsion form was prepared by mixing the following ingredients:

| | |
|---|---|
| Glyoxylic Acid | 10 wt. % |
| Cetearyl Alcohol | 2.18 wt. % |
| Dehydroxanthan Gum | 0.4 wt. % |
| Cetrimonium Methosulfate | 0.85 wt. % |
| Di-$C_{12}$-$C_{15}$ Dialkyl-dimethylammonium Chloride | 0.27 wt. % |
| Water | ad. 100 wt. % |

The pH was adjusted to 2.0 using sodium hydroxide.

Test Example

The feel of use of the composition of Examples 1 and 2 of the present invention as well as the resulting smoothness and the properties of the straightened hair were evaluated as follows.

A hairstreak weighing approximately 2 g was shampooed with a commercially available shampoo and blow dried. Subsequently, it was treated with approximately 1 g of a straightening composition and left at room temperature for about 15 min and dried with a hair drier. Afterwards, hair was treated with a flat iron having a surface temperature of 220° C. for 6 times. This was followed by washing the streaks with a commercially available shampoo and air-drying. The streaks were then visually and/or subjectively evaluated for the properties in Table 1 below by a hair stylist. The results of the evaluation are shown in the following table 1.

TABLE 1

| Criterion | Example 1 | Example 2 |
|---|---|---|
| Good Iron Gliding (during step e) | 3 | 3 |
| Natural Hair Feeling (uncoated after step e) | 4 | 4 |
| Less Volume in Hair (after step f) | 4 | 4 |
| Smoother hair structure (after step f) | 5 | 5 |
| Better combability (after step f) | 5 | 5 |

(1 = very poor result; 2 = poor; 3 = satisfactory; 4 = good 5 = very good result)

As apparent from the results, the compositions comprising the quaternary ammonium compound provide superior ease of use during the ironing, feel of use and smoothness and volume reduction of the straightened hair.

Example 3: Straightening Solution

| | % by weight |
|---|---|
| Glyoxylic acid | 10 |
| Tetranyl CO 40 | 4 |
| Sodium hydroxide | q.s. to pH 2.5 |
| Water | q.s. to 100 |

Example 4: Straightening Gel

| | % by weight |
|---|---|
| Glyoxylic acid | 5 |
| Tetranyl CO 40 | 3 |
| Xanthan gum | 1 |
| Sodium hydroxide | q.s. to pH 2.5 |
| Water | q.s. to 100 |

Example 5

| | % by weight |
|---|---|
| Glyoxylic acid | 5 |
| Polyquaternium-37 | 0.7 |
| Dibehenyldimonium chloride | 1.5 |
| Cetearyl alcohol | 4.0 |
| Behentrimonium chloride | 1.8 |
| Diemthicone | 0.3 |
| Water | to 100 |

Example 6

|  | % by weight |
|---|---|
| Glyoxylic acid | 10 |
| Hxdroxyethylcellulose | 1.1 |
| Sodium hydroxide | q.s. to pH 1.9 |
| Distearyldimonium chloride | 1.5 |
| Cetrimonium chloride | 0.5 |
| Ceteareth-30 | 1.5 |
| Cetearyl alcohol | 3.0 |
| Fragrance | 0.8 |
| Water | to 100 |

Example 7

|  | % by weight |
|---|---|
| Glyoxylic acid | 10 |
| Sodium hydroxide | q.s. to pH 2.0 |
| Ceteareth-30 | 2.5 |
| Cetearyl alcohol | 1.0 |
| Dicetyldimonium chloride | 0.8 |
| Dimethicone | 1.0 |
| PEG-40 hydrogenated castor oil | 0.5 |
| Fragrance | 0.8 |
| Water | to 100 |

Example 8

|  | % by weight |
|---|---|
| Glyoxylic acid | 10 |
| Polyquaternium-22 | 0.7 |
| Sodium hydroxide | q.s. to pH 2.0 |
| Quaternium-91 | 1.5 |
| Behenamidopropyltrimonium chloride | 0.9 |
| PEG-40 hydrogenated castor oil | 0.5 |
| Fragrance | 0.8 |
| Water | to 100 |

The invention claimed is:

1. A process for semi-permanent hair straightening, comprising the following steps performed in this order:
   (a) application of a hair straightening composition onto the hair;
   (b) leaving the composition on the hair for 10 to 60 minutes;
   (c) optionally rinsing off the hair;
   (d) drying the hair;
   (e) treating the hair with an iron having a surface temperature of 180±50° C.; and
   (f) optionally rinsing off and/or shampoo the hair and drying,
   wherein the hair straightening composition has a pH of 1 to 3 and is an emulsion comprising glyoxylic acid and/or a hydrate thereof and/or a salt thereof at a total concentration in the range of 2.5 to 20% by weight based on the weight of the total composition; and a quaternary ammonium salt of formula (III)

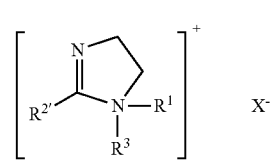

Formula (III)

wherein $R^1$ is selected from the group consisting of:
   optionally substituted $C_{8-22}$-alkyl;
   optionally substituted $C_{8-22}$-alkenyl;
   optionally substituted $C_{8-22}$-alkynyl;
   groups of the formula $R'—CO—NH—(CH_2)_n—$, wherein $R'$ is an optionally substituted $C_{8-22}$-alkyl, $C_{8-22}$-alkenyl or $C_{8-22}$ alkynyl group and n is an integer of 1 to 4; and
   groups of the formula $R'—CO—O—(CH_2)_n—$, wherein $R'$ and n are the same as defined above;
   the optional substituent(s) being selected from halogen, hydroxyl, amino and $C_1$-$C_4$ alkoxy;
$R^3$ represents an alkyl group with 1 to 4 carbon atoms, which may optionally be substituted with one or more hydroxyl groups or ethylene oxide and/or propylene oxide adducts thereof, the average addition number being in the range of 1 to 4;
$X^-$ represents an anion;
and $R^2$ represents a linear or branched $C_{8-22}$ alkyl, $C_{8-22}$ alkenyl or $C_{8-22}$ alkynyl group which may be optionally substituted with one or more substituents selected from halogen, hydroxyl, amino and $C_1$-$C_4$ alkoxy;
wherein the total content of the quaternary ammonium salt(s) is 0.01 to 15% by weight, based on the total of the composition;
wherein the hair straightening composition further comprises a silicone oil and/or a cationic polymer;
wherein the hair straightening composition further comprises one or more surfactants selected from cationic, nonionic, anionic and amphoteric ones;
wherein the hair straightening composition comprises at least one higher alcohol having 8 to 22 carbon atoms; and
wherein the combination with the application of a reducing composition or an alkaline relaxer is excluded.

2. The hair straightening composition process according to claim 1, wherein the hair straightening composition is a two-part composition comprising the parts A and B, which are provided for separate storage and for mixing prior to the application to the hair,
   wherein part A comprises said glyoxylic acid and/or a hydrate thereof and/or a salt thereof and part B comprises at least one of a fragrance, a surfactant or a conditioning component, and
   wherein the quaternary ammonium salt is contained in either or both of part A and part B.

3. The hair straightening process according to claim 1, wherein the cationic surfactant is a mono alkyl quaternary ammonium surfactant of the general formula

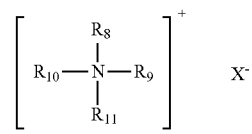

wherein $R_8$ is a saturated or unsaturated, branched or straight alkyl chain with 8-22 C atoms or $R_{12}$—CO—NH—$(CH_2)_n$— wherein $R_{12}$ is a saturated or unsaturated, branched or straight alkyl chain with 7-21 C atoms and n is an integer of 1-4, or $R_{12}$—CO—O—$(CH_2)_n$— wherein $R_{12}$ is a saturated or unsaturated, branched or straight alkyl chain with 7-21 C atoms and n is an integer of 1-4, and $R_9$, $R_{10}$ and $R_{11}$ are independent from each other, an alkyl group with 1 to 4 carbon atoms, hydroxyl alkyl chain with 1 to 4 carbon atoms, or ethoxy or propoxy group with a number of ethoxy or propoxy groups varying in the range of 1 to 4, and X is chloride, bromide, methosulfate or ethosulfate.

\* \* \* \* \*